US006659960B2

(12) United States Patent
Derksen et al.

(10) Patent No.: US 6,659,960 B2
(45) **Date of Patent: *Dec. 9, 2003**

(54) APPARATUS FOR RECORDING RESPIRATORY SOUNDS IN EXERCISING HORSES

(75) Inventors: Frederik J. Derksen, Bath, MI (US); Jennifer A. Brown, Lansing, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 10/126,298

(22) Filed: Apr. 19, 2002

(65) Prior Publication Data

US 2002/0156391 A1 Oct. 24, 2002

Related U.S. Application Data

(60) Provisional application No. 60/285,985, filed on Apr. 24, 2001.

(51) Int. Cl.[7] .................................................. A61B 5/08

(52) U.S. Cl. ........................ 600/529; 600/300; 600/586

(58) Field of Search ................................ 600/528, 529, 600/459, 481, 586, 532, 300, 587; 119/712, 729, 769, 792, 839, 174

(56) References Cited

U.S. PATENT DOCUMENTS

| | | | |
|---|---|---|---|
| 4,218,584 A | | 8/1980 | Attenburrow |
| 4,720,866 A | | 1/1988 | Elias et al. |
| 5,165,417 A | | 11/1992 | Murphy, Jr. |
| 5,503,141 A | | 4/1996 | Kettl et al. |
| 5,737,429 A | | 4/1998 | Lee |
| 5,853,005 A | * | 12/1998 | Scanlon ...................... 600/459 |
| 6,228,037 B1 | | 5/2001 | Derksen |
| 2002/0123699 A1 | * | 9/2002 | Lambert et al. ............ 600/586 |

OTHER PUBLICATIONS

Derksen et al., "Spectrogram Analysis of Respiratory Sounds in Exercising Horses," AAEP Proceedings, 45: 314–315 (1999).* http://www.nationalbridle.com, Online Catalog, pages regarding Bridles, Cavesons, and Hoods. (2003).* http://www.horsehoods.com/blinkers.html (2003).*

Seeherman, In: Current Therapy in Equine Medicine 4. robinston (ed), W. B. Saunders, Phil., pp. 404–407 (1997).

Ducharmè et al., In: Current Therapy in Equine Medicine 4. Robinson (ed), W.B. Saunders, Phil., pp. 415–418 (1997).

Kent, J. Voice 7: 97–117 (1993).

Lindell, Wilson Bull. 110: 368–374 (1998).

Hanggi and Schusterman, Anim. Behav. 48: 1275–1283 (1994).

Attenburrow et al., in Equine Exerc. Physiol. 27–32 (1990).

Attenburrow in Equine Vet. J. 10: 176–179 (1978).

Tetens et al., Am. J. Vet. Res. 57: 1668–1673 (1996).

Shappell et al., Am. J. Vet. Res. 49: 1760–1765.

Belknap et al., Am. J. Vet. Res. 51: 1481–1487 (1990).

Ehrlich et al., Vet. Surg. 24: 36–48 (1994).

Holcombe et al., Am. J. Vet. Res. 59: 504–508 (1998).

* cited by examiner

*Primary Examiner*—Charles A Marmor, II
(74) *Attorney, Agent, or Firm*—Ian C. McLeod

(57) ABSTRACT

A portable recording unit (10) for recording the upper airway respiratory sounds of an exercising horse to determine whether the horse suffers from an upper airway obstruction condition. The portable recording unit (10) comprises horse restraining apparatus (200) wherein microphone (12) is mounted on support (14), which is secured to nose-band (202) of horse restraining apparatus (200), and recorder (16). When horse restraining apparatus (200) is mounted onto head (102) of horse (100), microphone (12) is positioned forward to and between nostrils (108) of horse (100). Recorder (16) is fastened to neck (104) of horse (100) or is located at a remote location. Portable recording unit (10) allows recording of the upper airway respiratory sounds made by the exercising horse (100).

17 Claims, 9 Drawing Sheets

10 102 200 206 212 20 16 104 100 15 212 17 204 202 14 108 106 12A 13 12

APPARATUS FOR RECORDING RESPIRATORY SOUNDS IN EXERCISING HORSES

CROSS-REFERENCE TO RELATED APPLICATION

This application claims priority to Provisional Application Serial No. 60/285,985, filed Apr. 24, 2001.

STATEMENT REGARDING FEDERALLY SPONSORED RESEARCH OR DEVELOPMENT

Not applicable.

REFERENCE TO A "COMPUTER LISTING APPENDIX SUBMITTED ON A COMPACT DISC"

Not applicable.

BACKGROUND OF THE INVENTION (1) Field of the Invention

The present invention relates to an apparatus for recording the upper airway respiratory sounds of a horse during exercise of the horse to determine whether the horse suffers from an upper airway obstruction condition. In particular, the present invention relates to an apparatus comprising a horse restraining apparatus with a support member thereon which positions a microphone forward to and between (adjacent to) the horse's nostrils to detect respiratory sounds of the horse during exercise and which transmits the detected respiratory sounds to a recorder for analysis.

(2) Description of Related Art

Horses commonly suffer from several different upper airway obstructive diseases (conditions), including left laryngeal hemiplegia (LLH), dorsal displacement of the soft palate (DDSP), pharyngeal collapse, and entrapment of the epiglottis. Left laryngeal hemiplegia and DDSP are by far the most common causes of upper airway obstructions in horses and these conditions have an estimated prevalence of approximately 10% of horses. Left laryngeal hemiplegia is caused by a neuropathy of the left recurrent laryngeal nerve. This condition results in the paresis of the associated arytenoid cartilage. During exercise, this cartilage causes airway obstruction, respiratory noise, and exercise intolerance (Seeherman, In: *Current Therapy in Equine Medicine* 4. Robinson (ed), W. B. Saunders, Philadelphia, pp. 404–407 (1997)).

The cause of dorsal displacement of the soft palate is presently unknown. Experimentally, the disease is reproduced by blockade of the pharyngeal branch of the vagus nerve. Because this nerve branch runs in close proximity to the retropharyngeal lymph nodes, it is thought that in naturally occurring cases, DDSP is caused by infection of these lymph nodes and consequent damage to the nerve branch. Like in cases with LLH, DDSP causes airway obstruction, respiratory noise production and exercise intolerance in affected horses (Ducharme et al., In: *Current Therapy in Equine Medicine* 4. Robinson (ed), W. B. Saunders, Philadelphia, pp. 415–418 (1997)). In many cases, upper airway conditions can not be diagnosed in the resting horse as the conditions only occur during exercise. Upper airway obstructions are often associated with abnormal respiratory noise.

Respiratory sounds in exercising horses are difficult to evaluate because the trained observer is not always in an optimal location to hear the respiratory sounds. Furthermore, the respiratory sounds are obscured by extraneous noises such as hoof beats, wind noise, or sounds associated with treadmill operation. Presently, diagnostic methods are time consuming, highly technical, and expensive. The old method of diagnosing upper airway conditions in horses involves fiber optic endoscopy. In this technique, a fiber optic endoscope is inserted in the horse's nose and observations are made. To diagnose upper airway conditions that are only apparent during exercise, the horse is exercised on a high-speed treadmill and endoscopy is performed during exercise. This method is highly technical and can only be performed in referral centers.

In human medicine, spectrogram analysis of speech is a large field of study and practical applications of this field, including speech therapy and voice recognition, are now commonplace (Kent, J. Voice 7: 97–117 (1993)). In addition, spectrogram analysis of sound has been used in many animal species, including songbirds (Lindell, Wilson Bull. 110: 368–374 (1998)) and marine mammals (Hanggi and Schusterman, Anim. Behav. 48: 1275–1283 (1994)).

Respiratory sounds of horses have been recorded using a radiostethoscope such as that disclosed by Attenburrow et al., in Equine Exerc. Physiol._: 27–32 (1990) and in U.S. Pat. No. 4,218,584 to Attenburrow both of which describe a stethoscope for detecting and recording data from a horse while the horse is walking, trotting, cantering, jumping, and galloping. The invention includes a transducer, such as a microphone which is attached to the animal's skin adjacent the windpipe. The electrical output from the transducer is transferred to a radio transmitter mounted on the animal or its harness. The radio transmitter can transmit signals a distance from the horse to allow for monitoring the horse's breathing from a distance. While the respiratory sounds detected by the radiostethoscope placed over the trachea are analyzed using spectrogram analysis, the respiratory sounds do not directly relate to the respiratory sounds of exercising horses.

To correlate the respiratory sounds recorded by the radiostethoscope to inspiration or expiration of the exercising horse, Attenburrow in Equine Vet. J. 10: 176–179 (1978) further suspended a sub-miniature microphone just in front of one nostril. The microphone detects expiration by using the blast effect made by expired air upon the suspended microphone. The blast effect is the sound made by rushing expired air hitting the microphone which sounds much like the sound made by a strong wind hitting a microphone at an outdoor concert. Thus, the microphone is not detecting actual upper airway respiratory sounds made by the horse during respiration. Therefore, when a blast effect is detected by the microphone, the corresponding respiratory sound detected by the radiostethoscope was made during expiration. Conversely, when a blast effect is not detected by the microphone, the respiratory sound detected by the radiostethoscope was made during inspiration.

Also, of interest is U.S. Pat. No. 4,720,866 to Elias et al. which describes a method and apparatus for acquiring, analyzing, and displaying stethoscopic data using a microcomputer. The stethoscopic data come from lung sounds, not upper airway sounds as recorded in the invention described therein. The invention includes a means for providing an audio signal. The audio signal is pre-amplified and conditioned for application to a bank of fixed-center-frequency electronic filters. The output of each filter is sampled and converted to digital form. The output is then processed in a computer for analysis and display on a CRT screen or recording in a hard copy device.

U.S. Pat. No. 5,165,417 to Murphy, Jr. describes a diagnostic method and apparatus for detecting breathing abnormalities in humans to diagnose lung (not upper airway) disorders. The system includes means for receiving the sound signal from the patient, means for conditioning the sound signal to attenuate normal sounds, and means for storing a sample sound signal. The system may also include means for digitizing the sound signal, means for amplifying the sound signal, means for determining an average signal value of at least a portion of the sound signal, and means for generating a threshold value based on that average value. Further included may be means for sequentially comparing the sound waves with the predetermined time interval to identify an initial deflection wave having a duration falling within the time interval, means responsive to the means for sequentially comparing the sound waves for sequentially comparing the sound waves following the initial deflection wave to the threshold value, and means for identifying an adventitious sound occurring within the sound signal only when a plurality of consecutive sound waves including the initial deflection wave have an amplitude at least as large as the threshold value.

U.S. Pat. No. 5,737,429 to Lee describes a portable, visible, and audible stethoscope. The stethoscope includes a sound absorbing cup having a microphone and an output device. In use, the sounds from the human body are converted into electrical signals by microphone. The electrical signals are amplified in the output device and supplied to the speaker of the output device to produce an audio signal. The amplified electrical signals are also supplied to the oscilloscope to produce a graph representing the electrical signals.

Only of minimal interest is U.S. Pat. No. 5,503,141 to Kettl et al. which shows a microphone mounting structure which permits conversion of a conventional respirator into a sound amplifying respirator. The invention uses a microphone responsive to oral sounds within the respiratory mask and produces electrical signals indicative of these oral sounds. The system also includes an amplification circuit which provides output sounds representative of the oral sounds which the microphone detects within the mask.

In light of the prior art, there remains a need for an apparatus for recording the upper airway respiratory sounds of a horse during exercise which is portable and easy to use and which allows the recorded respiratory sounds to be analyzed for upper airway obstructive diseases.

SUMMARY OF THE INVENTION

The present invention provides an apparatus for recording the upper airway respiratory sounds of a horse during exercise which is portable and easy to use and which allows the recorded respiratory sounds to be analyzed for upper airway obstructive diseases either after exercise or in real time.

In particular, the present invention provides an apparatus for recording respiratory sounds of an exercising horse which comprises (a) a microphone with a head which detects respiratory sounds at close proximity; (b) a horse restraining apparatus comprising a nose-band and a cheek-piece with a top for going behind and around the ears of the horse both mountable on the head of the horse wherein the horse restraining apparatus includes a support means for the microphone mounted on the nose-band of the horse restraining apparatus wherein the support means allows the head of the microphone to be positioned between nostrils of the horse without touching the horse so that the respiratory sounds at close proximity to the nostrils of the horse are detected; and (c) a recording means for recording the respiratory sounds from the microphone at close proximity to the nostrils of the horse wherein the recording means squelches other sounds at a distance from the nostrils.

In a further embodiment of the apparatus, a wire for transmitting the respiratory sounds detected by the microphone to the recording means extends from the microphone to the recording means along a path which is parallel to the support means mounted on the nose-band of the horse restraining apparatus and is parallel to the nose-band and the cheek-piece to the top of the cheek-piece and which extends from the top piece to the recording means.

In a further embodiment of the apparatus, the support means is a tube defined by at least one wall forming the tube in which the wire for transmitting the respiratory sounds extends therethrough.

In a further still embodiment of the apparatus, the microphone is unidirectional.

In a further still embodiment of the apparatus, the recording means has a compression circuit which allows for a constant recording level of the sounds at close proximity to the nostrils of the horse.

In a further still embodiment of the apparatus, the microphone includes a wireless transmitter for transmitting the respiratory sounds to a wireless receiver in the recording means.

In a further still embodiment of the apparatus, the microphone includes a wireless transmitter for transmitting the respiratory sounds to a wireless receiver in a computer for analyzing the respiratory sounds in real time.

The present invention further provides a method for recording and analyzing respiratory sounds of an exercising horse to detect an airway condition which comprises (a) providing an apparatus for analyzing respiratory sounds of an exercising horse which comprises (1) a microphone with a head which detects respiratory sounds at close proximity; (2) a horse restraining apparatus comprising a nose-band and a cheek-piece with a top for going behind and around the ears of the horse both mountable on the head of the horse wherein the horse restraining apparatus includes a support means for the microphone mounted on the nose-band of the horse restraining apparatus wherein the support means allows the head of the microphone to be positioned between nostrils of the horse without touching the horse so that the respiratory sounds at close proximity to the nostrils of the horse are detected; and (3) a recording means for recording the respiratory sounds from the microphone at close proximity to the nostrils of the horse and squelches other sounds at a distance from the nostrils; (b) mounting the head of the microphone adjacent to the nostrils of the horse; (c) recording the respiratory sounds detected by the head of the microphone with the recording means; and (d) analyzing the respiratory sounds recorded on the recording means to detect the condition.

In a further embodiment of the method, a wire for transmitting the respiratory sounds detected by the microphone to the recording means extends from the microphone to the recording means along a path which is parallel to the support means mounted on the nose-band of the horse restraining apparatus and is parallel to the nose-band and the cheek-piece to the top of the cheek-piece and which extends from the top piece to the recording means.

In a further still embodiment of the method, the support means is a tube defined by at least one wall forming the tube in which the wire for transmitting the respiratory sounds extends therethrough.

In a further still embodiment of the method, the microphone includes a wireless transmitter for transmitting the respiratory sounds to a wireless receiver in the recording means.

In a further still embodiment of the method, the microphone includes a wireless transmitter for transmitting the respiratory sounds to a wireless receiver in a computer for analyzing the respiratory sounds in real time.

In a further still embodiment of the method, the analysis is for laryngeal hemiplegia and dorsal displacement of the soft palate.

In a further still embodiment of the method, a computer program produces a graph of the respiratory sounds for analyzing in step (d).

The object of the present invention is to provide an easy and inexpensive method and apparatus for diagnosing upper airway obstruction conditions in exercising horses.

That and other objects of the present invention will become increasingly apparent with reference to the following drawings and examples of embodiments which satisfy the objects of the present invention.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

During exercise, horses make upper airway respiratory sounds (hereinafter, "respiratory sounds"). In horses with different airway obstruction conditions, these upper airway respiratory sounds change and importantly, these changes in upper airway respiratory sounds are characteristic for each upper airway obstruction condition. The portable recording unit of the present invention comprises a horse restraining apparatus which comprises a nose-band and a cheek-piece with a top for going around and behind the ears of the horse to keep the nose-band from slipping off the nose (a preferred horse restraining apparatus is a cavesson), a microphone (preferably unidirectional) secured to a support which is mounted on the nose-band, and a recorder (preferably with compression circuitry). The portable recording unit of the present invention provides an easy and inexpensive method and apparatus for diagnosing upper airway obstruction conditions in exercising horses. The portable recording unit of the present invention is an improvement over the portable recording unit taught in commonly owned U.S. Pat. No. 6,228,037 to Derksen.

Figure 1:
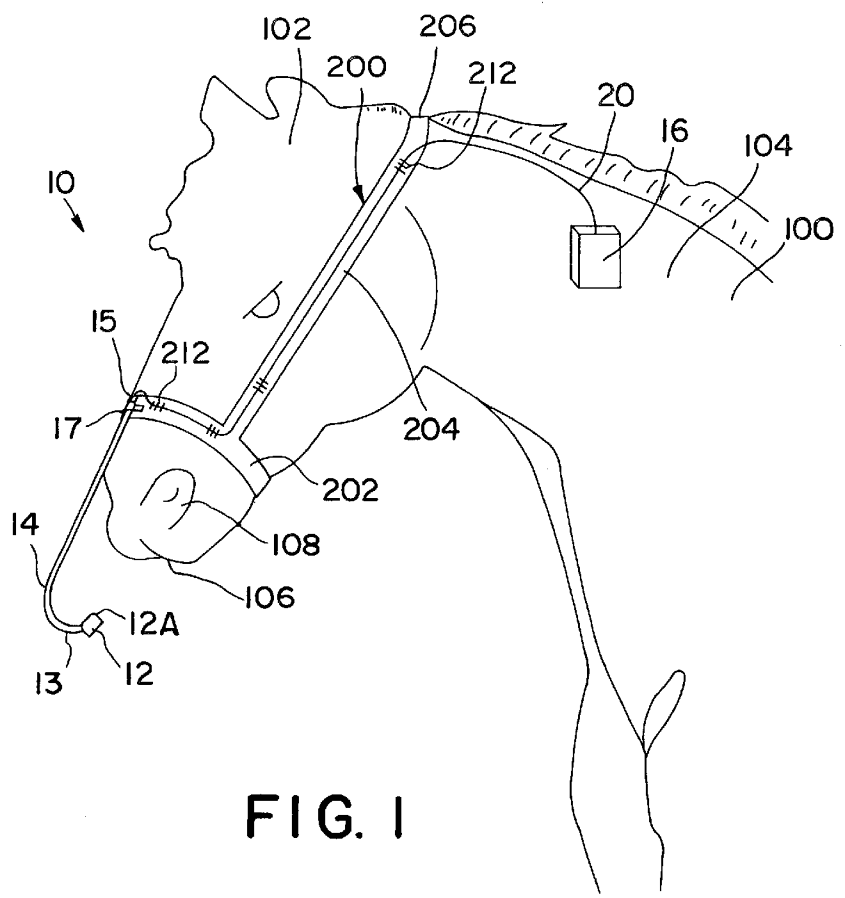
FIG. 1 is a side view of the portable recording unit 10 comprising horse restraining apparatus 200 with microphone 12 and support 14 secured to nose-band 202 of horse restraining apparatus 200.
Figure 2:
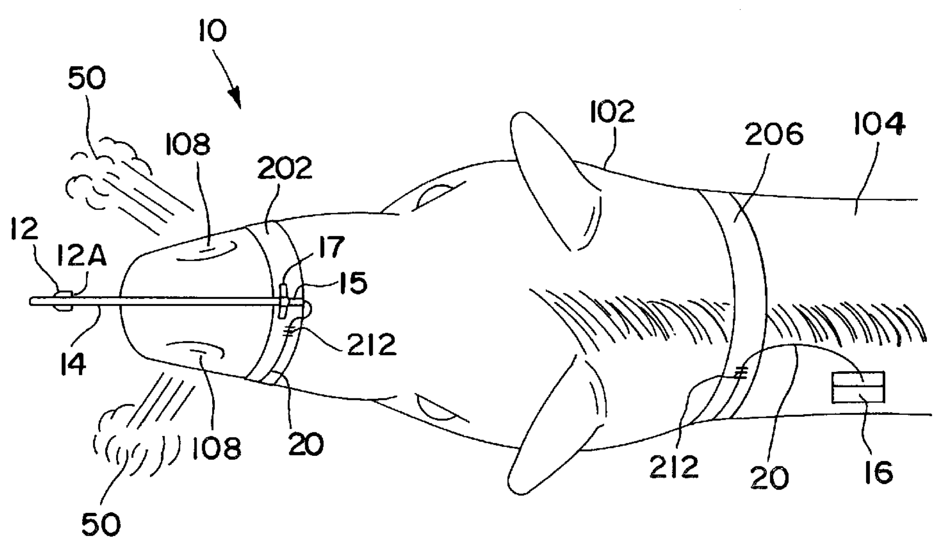
FIG. 2 is an overhead view of horse 100 with portable recording unit 10 mounted on the head 102 thereof. The Figure shows that microphone 12 is positioned forward and between the nostrils 108 of the horse 100 so as to be outside the path of the air 50 expired from the horse's nostrils 108.

Shown in FIGS. 1 and 2 is an embodiment of the portable recording unit 10 which comprises a horse restraining apparatus 200 (the Figure shows a cavesson, which is the preferred horse restraining apparatus), a microphone 12 (preferably unidirectional), and a recorder 16 (preferably with compression circuitry). The combination of a unidirectional microphone and the compression circuitry filters out extraneous noises such as hoof beats, wind noise, and sounds associated with treadmill operation.

Figure 3A:
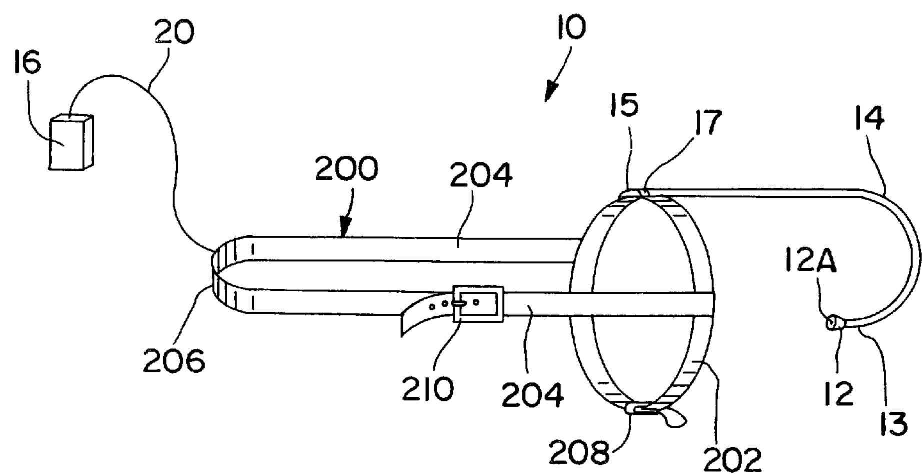
FIG. 3A shows a right-side view of the portable recording unit 10 comprising horse restraining apparatus 200.

The horse restraining apparatus 200 comprises a nose-band 202 and a cheek-piece 204 with a top 206. The top 206 of the cheek-piece 204 and is formed when the cheek-piece 204 is fitted around the head 102 of the horse 100 and secured with buckle 210 (FIG. 3A). The microphone 12 is secured to the distal end 13 of a flexible or bendable support 14, preferably the support 14 is a flexible or bendable conduit. The proximal end 15 of the bendable support is secured to nose-band 202 of the horse restraining apparatus 200 by bracket 17.

In a preferred embodiment, the horse restraining apparatus is a cavesson. Traditionally, cavessons are made from leather, however, nylon cavessons are also available. A cavesson may or may not have a metal nose-band. The recording unit 10 can comprise any manufacture of cavesson. Furthermore, while a cavesson is shown in the Figures, one skilled in the art will readily appreciate that a bridle or halter with a nose-band can be substituted for or combined with the cavesson without departing from the spirit of the present invention. Therefore, the term "horse restraining apparatus" as used herein includes leather, nylon, metal nose-band, lungeing, and bitting cavessons and other horse restraining equipment such as bridles, bitless bridles, halters, and the like so long as the horse restraining apparatus has a nose band to which the support 14 can be mounted and a cheek-piece that goes around the horse's ears as shown in the Figures to keep the nose-band from sliding off the nose.

Figure 6:
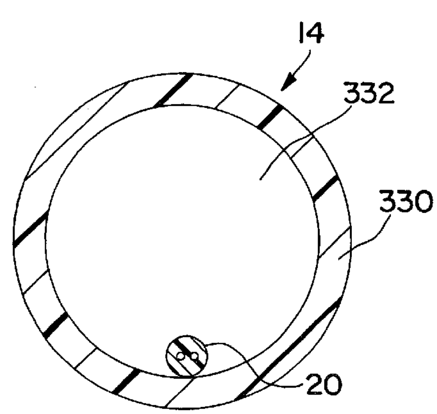
FIG. 6 shows a cross-section view of support 14 viewed along line 6 of FIG. 4 showing sidewall 330 defining internal space 332 and wire 20.

In the embodiment shown, the support 14 is a flexible or bendable conduit and the microphone 12 is operably connected to recorder 16 by wire 20. The wire 20 travels from the microphone 12 through the flexible or bendable support 14 (FIG. 6 shows a cross-section view of the support 14 showing inner space 332 for wire 20 to travel through) and then exits the support 14 at its proximal end 15 wherein it then travels along a pathway parallel the nose-band 202 to the cheek-piece 204 and then along a pathway parallel the cheek-piece 204 to the top 206 wherein it then travels along the neck 104 of the horse 100 to the recorder 16. The wire is fastened to nose-band 202 and cheek-piece 204 by a plurality of fastening means 212 such as stitching, clamps, tacks, adhesive, or the like.

As shown by FIGS. 1 and 2, when the recording unit 10 is mounted on the head 102 of the horse 100, the microphone 12 of the portable recording unit 10 is positioned by the support 14 to be adjacent the horse's nostrils 108, i.e., forward of the horse's nose 106 and between the horse's nostrils 108, and the recorder 16 is mounted on the neck 104 of the horse 100. The microphone 12 and the recorder 16 can be analog, digital, or combination thereof.

Figure 4:
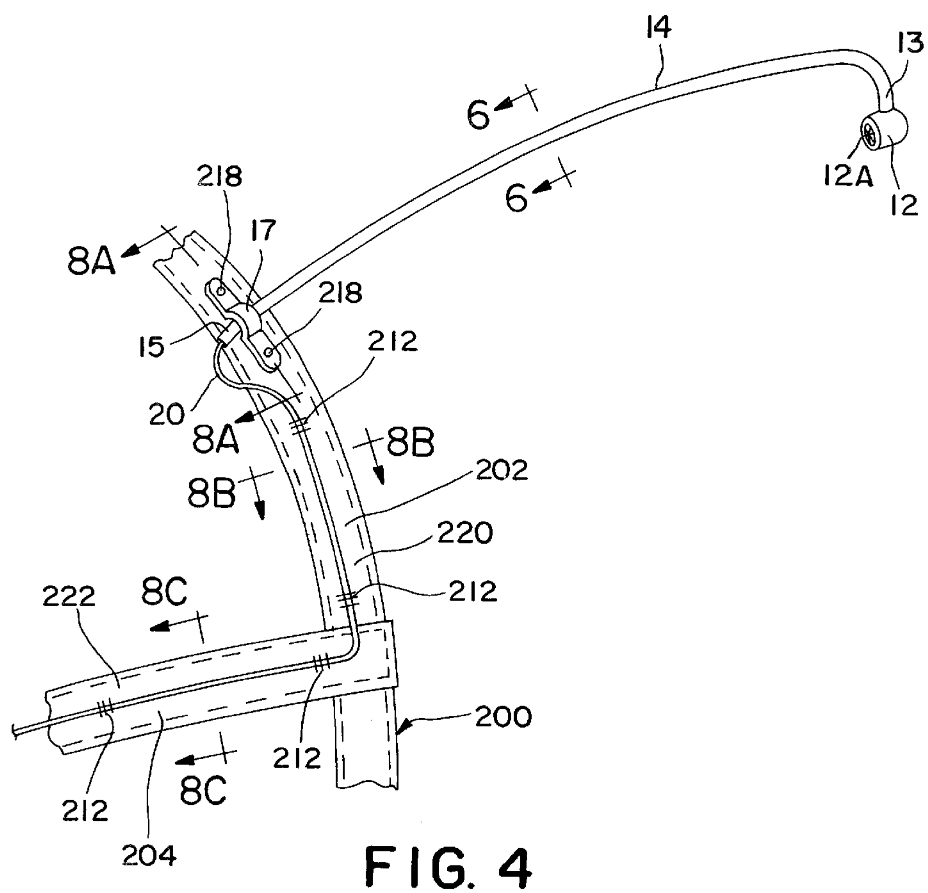
FIG. 4 shows the section of the nose-band 202 to which the support 14 is secured with bracket 17 and cheek-piece 204 of the horse restraining apparatus 200.

To position the microphone 12 forward to and between the nostrils 108 of the horse 100, i.e., adjacent to the nostrils 108, the microphone 12 is secured to the distal end 13 of the support 14 Preferably, the microphone 12 and the support 14 are a single unit. The microphone 12 is positioned such that the head 12A of the microphone 12 extends inward toward the proximal end 15 of the support 14. The proximal end 15 of the support 14 is then secured to the nose-band 202 of the horse restraining apparatus 200 by bracket 17 which is in turn secured to the nose-band 202 by a securing means 218 such as bolts, rivets, tacks, stitching, adhesive, or the like (FIG. 4).

In particular embodiments, the support 14 or the proximal end 15 of the support 14 is metal which enables the support 14 to be secured to the bracket 17 by welding. In other embodiments, the support 14 is secured at the proximal end 15 by bracket 17 wherein the bracket 17 tightly clamps the proximal end 15 of the support 14 to the nose-band 202.

The horse restraining apparatus 200 is then mounted on the head 102 of the horse 100 such that the support 14 is cantilevered over the nose 106 of the horse 100 and extended beyond the nose 106 a sufficient distance to place the microphone head 12A of microphone 12 at the distal end 13 of the support 14 in front of the nose 106 and between the nostrils 108. The proximal end 15 of the support 14 is secured to horse restraining apparatus 200 with the bracket 17.

An important element of the recording unit 10 is illustrated in FIG. 2. As shown in FIG. 2, the microphone 12 is positioned such that while the head 12A of the microphone 12 is in close proximity to the nostrils 108 of the horse 100 to enable it to detect the horse's respiratory sounds, it is not directly in front of either nostril 108 of the horse 100. The microphone 12 is not directly in front of either nostril 108 to prevent the microphone head 12A from detecting a blast effect which would result if the expired air 50 from the nostrils 108 of the horse 100 were to contact the microphone head 12A. The blast effect would interfere with detecting the respiratory sounds. In contrast, Attenburrow in Equine Vet. J. 10: 176–179 (1978) places a microphone directly in front of a nostril for the sole purpose of detecting the blast effect which is then used to determine whether the respiratory sounds detected by the radiostethoscope were made during expiration or during inspiration.

Figure 3B:
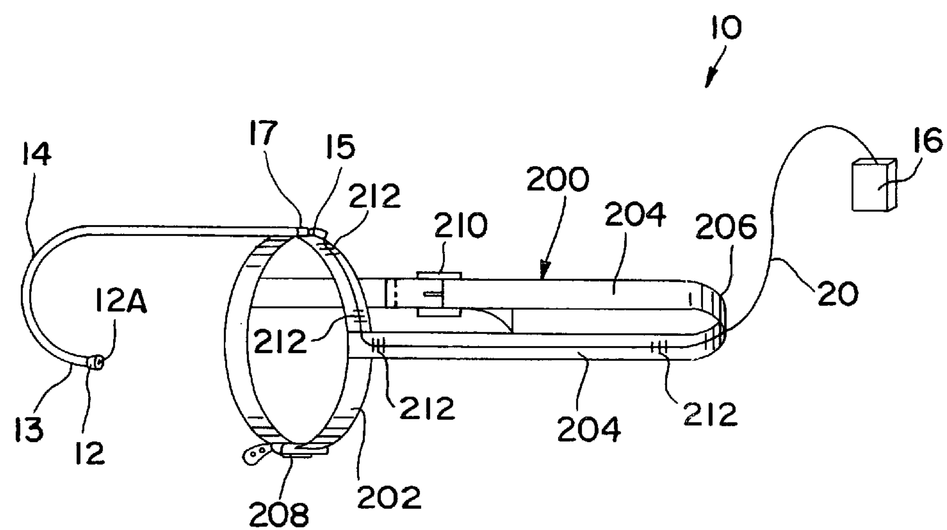
FIG. 3B shows a left-side view of the portable recording unit 10 comprising horse restraining apparatus 200.

FIG. 3A shows a right-side view of the recording unit 10 and FIG. 3B shows a left-side view of recording unit 10. The Figures show horse restraining apparatus 200 (the Figure shows a cavesson which is preferred) with nose-band 202 and cheek-piece 204 and top 206. The Figures show the support 14 with microphone 12 secured to the distal end 13 of the support 14 so that the microphone head 12A is facing the proximal end 15 of the support 14 and shows the proximal end 15 of the support 14 secured to the nose-band 202 by clamp 17. Exiting from the proximal end 15 of the support 14 is wire 20 which operably connects the microphone 12 to the recorder 16. Wire 20 is fastened to the nose-band 202 and cheek-piece 204 by fastening means 212. The nose-band 202 is secured to the horse's nose 106 using the buckle 208 and the cheek-piece 204 is secured to the horse's head 102 using the buckle 210. When the horse restraining apparatus 200 is fitted to the horse's head with the cheek-piece 204 looped around the horse's head and secured with buckle 210, the central section of the cheek-piece 204 forms the top 206. FIG. 3B shows that wire 20 travels along a path parallel to the nose-band 202 and the cheek-piece 204 and then from the top 206 to the recorder 16.

FIG. 4 shows a close-up view of the support 14 secured to the nose-piece 202 of the horse restraining apparatus 200 of the portable recording unit 10. The Figure shows support 14 with microphone 12 attached to distal end 13 and secured at its proximal end 15 to the nose-band 202 by clamp 17 which is secured to the nose-band 202 with securing means 218. The microphone 12 is positioned such that its head 12A is directed towards the proximal end 15 of the support 14. Wire 20 exits the proximal end 15 of the support 14 and travels along the nose-band 202 and the cheek-piece 204. The wire is secured in place by a plurality of fastening means 212.

In particular embodiments not shown, the support 14 can have a telescopic or other slidable construction which allows the length of the support 14 to be adjusted. However, it is preferable that the support 14 comprise a flexible or bendable conduit. As shown in FIGS. 1 and 2, the bendable or flexible conduit support 14 enables the position of the head 12A of the microphone 12 to be adjusted to be just forward of the nose 106 of the horse 100 but without touching the nose 106 merely by bending the support into the desired position. By positioning the microphone head 12A just forward of the nose 106, a "tight-mike" technique can be used to record the respiratory sounds at the nostrils 108 of the exercising horse 100. Furthermore, it is preferable that the flexible or bendable conduit be a tube with the wire 20 from the microphone 12 traversing therethrough and exiting at the proximal end 15 of the support 14. FIG. 6 shows a cross-section of the flexible or bendable conduit support 14 along line 6 of FIG. 4. FIG. 6 shows side wall 330 of support 14 forming a tube with internal space 332 and wire 20 therein.

As shown in FIGS. 1 and 2, the recorder 16 is fastened to the neck 104 of the horse 100 by any well known fastening means such as elastic tape, adhesive tape, a belt, or a strap. In this embodiment, since the entire recording unit 10 is mounted on the horse 100, the test can be performed anywhere the horse 100 can exercise. In a further embodiment, the recorder 16 is fastened to a saddle (not shown) on the back of the horse 100, secured in a pocket in the saddle (not shown), a harness (not shown) on the horse 100, a sulky (not shown) pulled by the horse 100, or fastened to the top 206 of the cheek-piece 204. In an alternative embodiment, the horse 100 is positioned on a high speed treadmill of a type commonly used by veterinarians and horse owners to exercise a horse such as the treadmill 110 shown in FIG. 7 and the recorder 16 can be attached to the treadmill 110.

The recording unit of commonly owned U.S. Pat. No. 6,228,037 to Derksen has a microphone operably connected to a recorder with a wire for transmitting respiratory sounds received by the microphone to the recorder. The wire hangs along the side of the head of the horse. In practice, the hanging wire is distracting to the horse which in turn can effect the breathing of the horse during recording thereby causing aberrant respiratory sounds. Furthermore, because the hanging wire must have some slack to allow the horse to move its head naturally during exercise, the hanging wire will sway to and fro and bounce up and down during exercise. The swaying and bouncing wire can spook the horse. The present invention solves the hanging wire problem inherent to the recording unit of U.S. Pat. No. 6,228,037 to Derksen.

In the recording unit 10 of the present invention, the wire is an integral part of the horse restraining apparatus 200. As shown in FIGS. 1–4, the wire 20 connecting the microphone 12 to the recorder 16, extends from the microphone 12 through the support 14 to the nose-band 202 of the horse restraining apparatus 200. The wire 20 exits the support 14 and travels along a path parallel to the nose-band 202 to the cheek-piece 204 of the horse restraining apparatus 200, along a path parallel to the cheek-piece 204 to the top 206 of the cheek-piece 204 of the horse restraining apparatus 200, and then from the top 206 of the cheek-piece 204 to the recorder 16 which is fastened to the neck 104 of the horse 100. The wire 20 is fastened to the surface 220 of the nose-band 202 (FIG. 4) and the surface 222 of the cheek-piece 204 (FIG. 4) or within a groove or channel (not shown) in the surface 220 and 222 of the aforementioned components of the horse restraining apparatus 200.

Figure 8A:
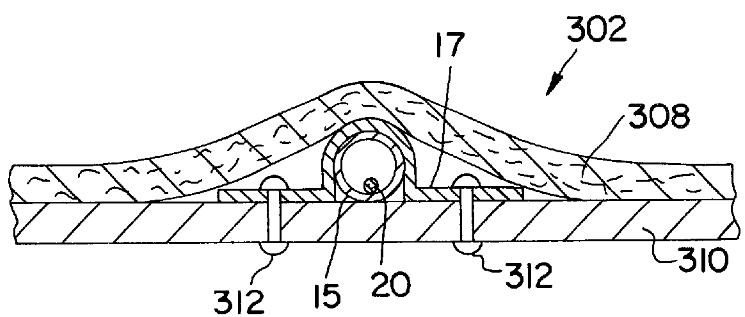
FIG. 8A shows a cross-section view of a two-piece nose-band 302 as it would appear if viewed along line 8A of FIG. 4.
Figure 8B:
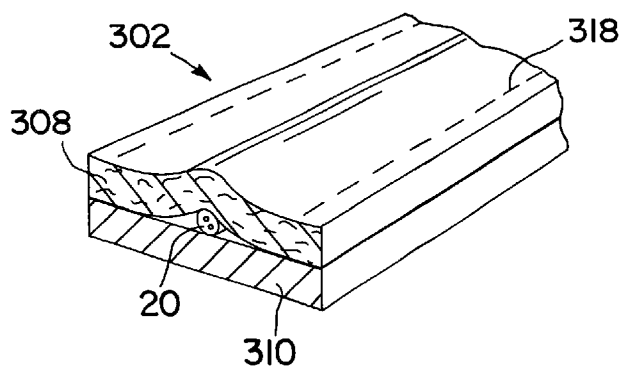
FIG. 8B shows a cross-section perspective view of a two-piece nose-band 302 as it would appear if viewed along line 8B of FIG. 4.
Figure 8C:
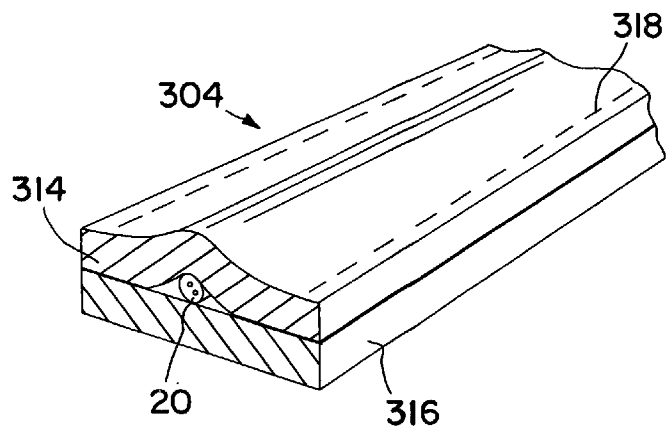
FIG. 8C shows a cross-section perspective view of a two-piece cheek-piece 304 as it would appear if viewed along line 8C of FIG. 4.

FIGS. 8A, 8B, and 8C show an embodiment of the recording unit 10 wherein the nose-band 202 and the cheek-piece 204 of the horse restraining apparatus 200 comprises two pieces with the wire 20 sandwiched therebetween. The two-piece construction protects the wire 20 from damage. FIG. 8A shows a cross-section view of a two-piece nose-band 302 with a top piece 308 and a bottom piece 310 as it would appear if viewed along line BA of FIG. 4. Between the top piece 308 and the bottom piece 310 is bracket 17 securing the proximal end 15 of the support 14 with wire 20 therein. The bracket 17 is shown secured to the bottom piece with rivets 312 as the securing means 218. FIG. 8B shows the two-piece nose-band 302 with a top piece 308 and a bottom piece 310 with wire 20 sandwiched therebetween as it would appear if viewed along line 8B of FIG. 4. FIG. 8C shows a cross-section perspective view of FIG. 4 of a two-piece cheek-piece 304 with a top piece 314 and a bottom piece 316 with wire 20 sandwiched therebetween as it would appear if viewed along line 8C of FIG. 4. FIGS. 8B and 8C show the top and bottom pieces held together with stitching 318, however, other means such as adhesive, rivets, tacks, and the like can be used to hold the top and bottom pieces together. Both the top and bottom pieces can be made from leather, nylon, an other material such as rubber, plastic, metal, or cloth, or a combination thereof. For example, the top and bottom pieces can both be made from leather or the bottom piece can be made from leather and the top piece made from another material such as nylon.

The wire 20 has standard plugs or connectors at both ends (not shown) for plugging the ends of wire 20 into the sockets (not shown) of the microphone 12 and the recorder 16 to operably connect the microphone 12 to the recorder 16. Alternatively, one end of the wire 20 is directly attached to the circuitry of the microphone 12 (not shown) and the other end of the wire 20 has a plug (not shown) which is plugged into a socket (not shown) in the recorder 16. As used herein, the term "wire" includes not only metal wire for electrical transmission of the respiratory sounds but also fiber optic wires for light transmission of the respiratory sounds.

The support 14, which preferably is a flexible or bendable conduit, can be manufactured from a material which includes but is not limited to metal, metal covered with a plastic, plastic, rubber, reinforced plastic or rubber, or combinations thereof. It is preferable that the support be flexible or bendable such that it can be manually bent into a plurality of stable configurations. For example, the support 14 is a flexible conduit comprising a polymeric material which is used to make the boom that supports the microphone of telephone headsets such as those commonly used by telephone marketers and receptionists. It is preferable that the proximal end of such a support 14 be flanked with a metal cover which is then covered with a polymeric material to form a tight bond between the flexible conduit and the flanking metal cover (not shown). The metal cover protects the proximal section of the support 14 and can extend the proximal end 15 of the support 14 beyond the proximal end of the flexible conduit comprising the support 14. The metal at the proximal end 15 of the support 14 is left exposed to enable the support 14 to be welded to the bracket 17 on the nose-band 202.

In a still further embodiment, the transmission of respiratory sounds from the microphone 12 to the recorder 16 is by wireless transmission. Wireless transmission can be accomplished by including a wireless transmitter operably connected to the microphone 12 to transmit the respiratory sounds and a wireless receiver operably connected to the recorder 16 to receive the respiratory sounds instead of using the wire 20 to transmit the respiratory sounds from the microphone 12 to the recorder 16. When a wireless transmitter is used for transmitting the respiratory sounds to a recorder with a wireless receiver therein, the recorder with the wireless receiver therein can be in a location remote from the exercising horse 100. Therefore, when respiratory sounds are transmitted to a recorder by a wireless means, the horse restraining apparatus 200 need only comprise a microphone with a wireless transmitter therein or mounted on the horse and support 14 with microphone 12 secured to the nose-band 202.

Figure 7:
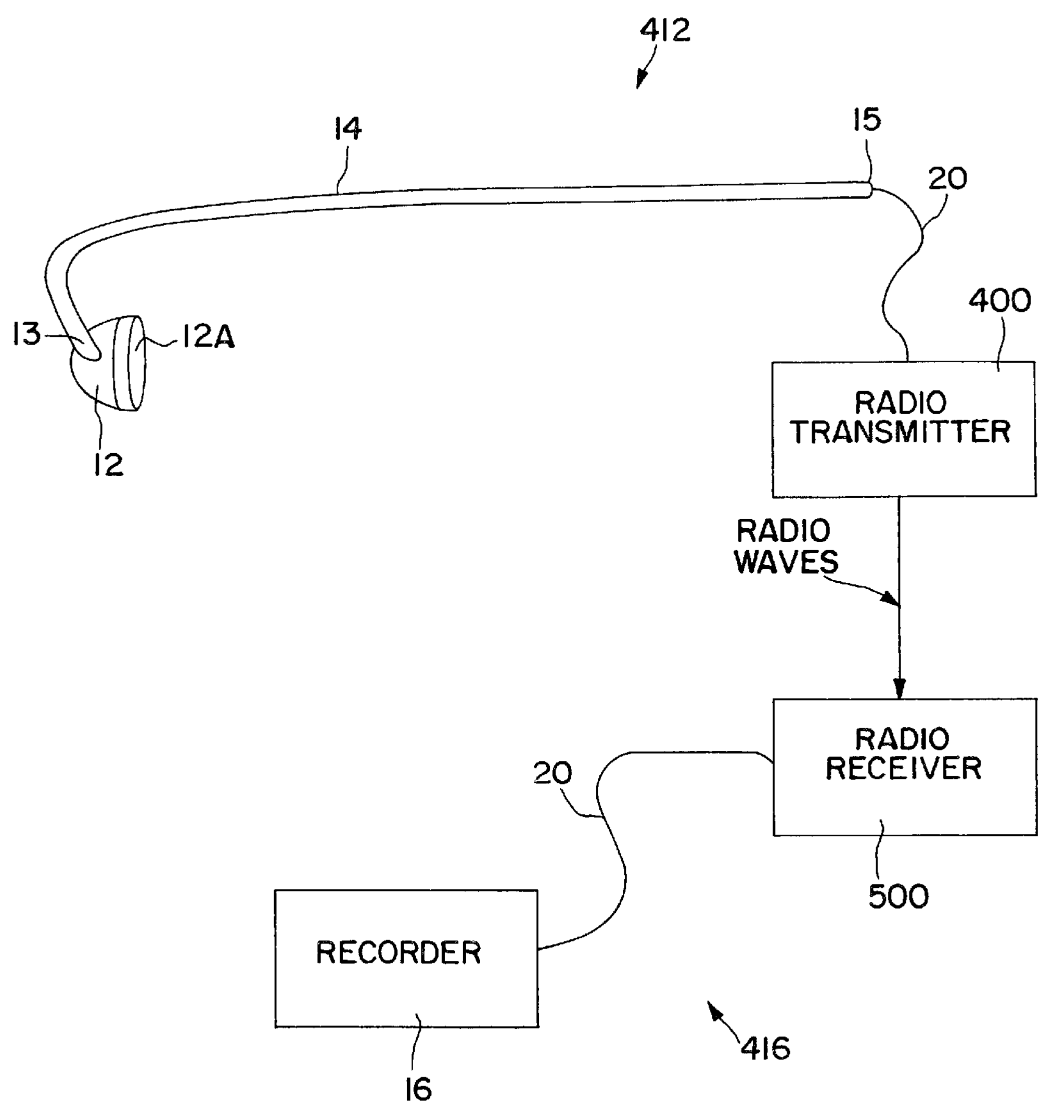
FIG. 7 shows wireless microphone 412 comprising microphone 12 secured to the distal end 13 of support 14 wherein the microphone 12 is operably connected by wire 20 to transmitter 400 and wireless recorder 416 comprising recorder 16 operably connected to receiver 500 by wire 20.

FIG. 7 shows an embodiment of a wireless microphone 412 comprising a microphone 12 with head 12A mounted on the distal end 13 of support 14. The microphone 12 is operably connected to a transmitter 400 by wire 20 which exits the support 14 at its proximal end 15. Also shown is a wireless recorder 416 comprising a recorder 16 operably connected by wire 20 to a receiver 500 which receives the transmissions from the transmitter.

Wireless transmission of the respiratory sounds enhances the utility of the present invention because it eliminates the need for wires and also allows for real time analysis of the respiratory sounds as the horse is exercising. Real time analysis enables the exercise regimen to be altered in response to particular respiratory sounds at the time the respiratory sounds are being made. Thus, while the horse 100 is exercising, the respiratory sounds, which are detected by a microphone 12 operably connected to a wireless transmitter, are transmitted to a wireless receiver operably connected to a computer comprising a computer program for analyzing the respiratory sounds and displaying the results of the analyzed respiratory sounds on a computer screen or a printer for a hard copy in real time. Wireless transmission of the respiratory sounds can be by radio, microwave, light, infrared light, ultrasonic sound, or other wireless means.

Figure 5:
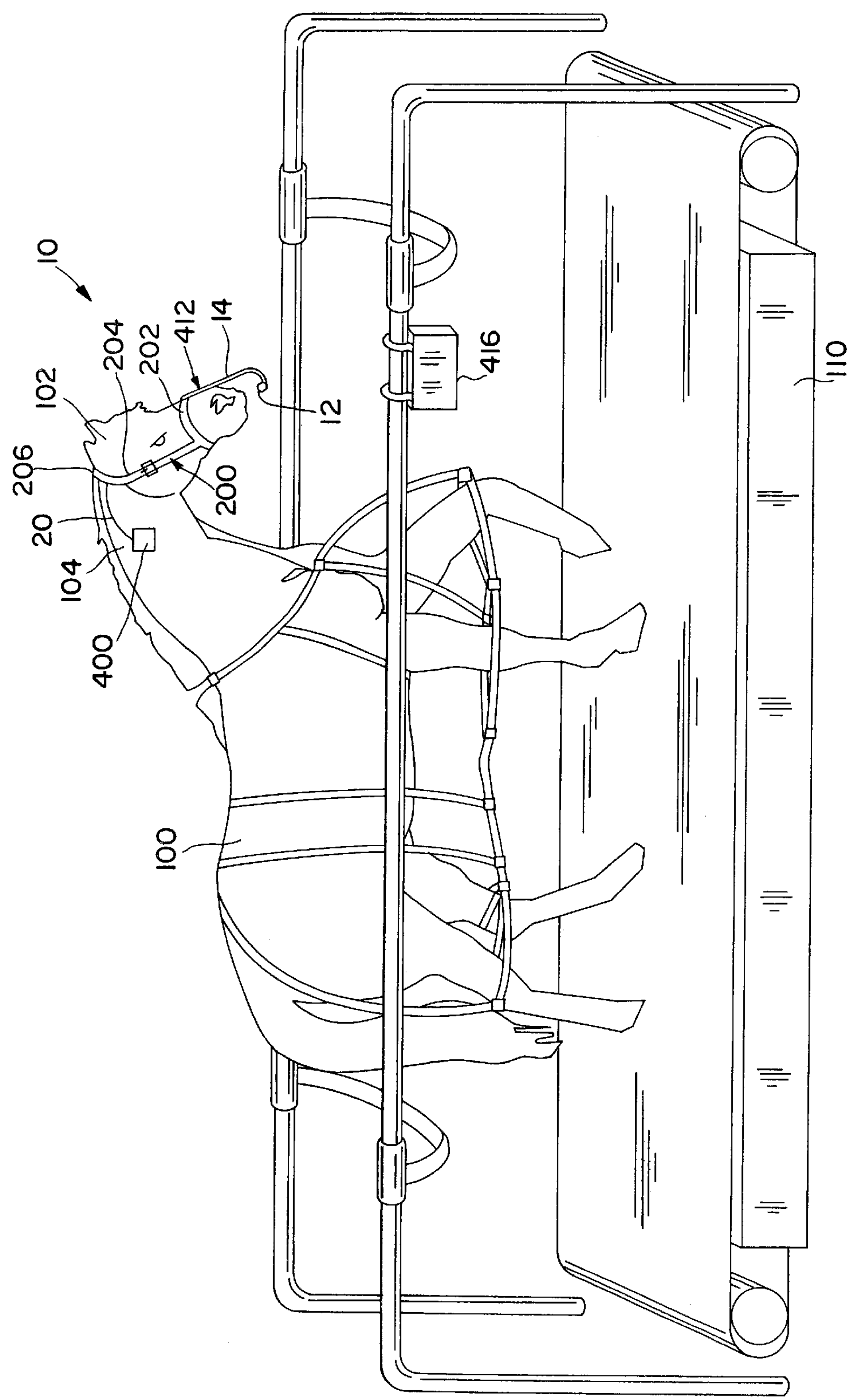
FIG. 5 shows a perspective view of the horse 100 exercising on a treadmill 110 with the respiratory sounds monitored by portable recording unit 10 comprising wireless microphone 412 and wireless recorder 416.

FIG. 5 shows a wireless embodiment of the recording unit 10 for recording the respiratory sounds made by a horse while being exercised on a treadmill. FIG. 5 shows horse 100 on treadmill 110 wherein the horse 100 has on its head 102 a portable recording unit 10 comprising a horse restraining apparatus 200 with a wireless microphone 412 as shown in FIG. 7 fastened to nose-band 202 of horse restraining apparatus 200 and wireless recorder 416 (with the receiver an integral component of the receiver) fastened to treadmill 110 with bracket 18. The wireless transmitter 400 is fastened to the neck 104 of the horse 100 and is operably connected to the microphone 12 by wire 20.

In a further embodiment (not shown), the microphone and recorder or wireless transmitter are of a sufficiently reduced size that both can be attached to the support 14 which is secured to the horse restraining apparatus 200. In particular embodiments, a single unit comprising both a microphone and a recorder or wireless transmitter is attached to the support 14. In further embodiments, the recording unit 10 comprises two microphones for detecting respiratory sounds, a microphone for detecting the respiratory sounds from each nostril 108 of the horse 100, and the recorder contains two channels for recording the respiratory sounds, a channel for each microphone.

In any one of the above embodiments, after the respiratory sounds are recorded on the recorder and the data transferred to a personal computer (not shown) or transmitted in real time to a recorder containing a radio receiver and which is operably connected to a computer (not shown) or to a radio receiver operably connected to a computer (not shown), the sounds are analyzed using commercially available spectrum analysis computer software. Spectrum analysis allows plotting of time, frequency, and sound amplitude of the respiratory sounds to give easily recognizable patterns.

Figure 9:
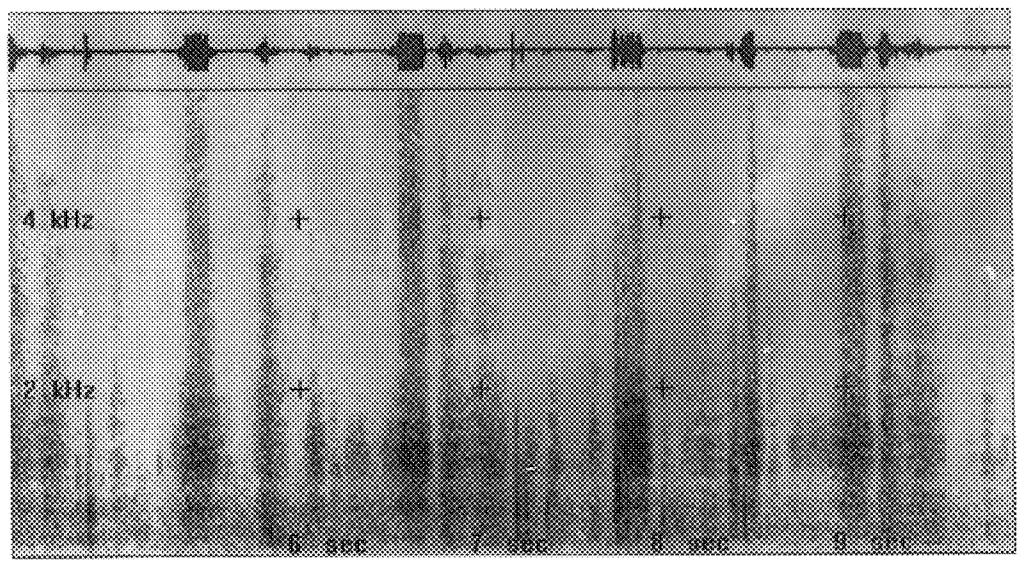
FIG. 9 shows a spectrogram of the upper respiratory sounds of a horse 100 with left laryngeal hemiplegia (LLH) exercising on a treadmill 110 at a speed corresponding to its maximum heart rate.
Figure 10:
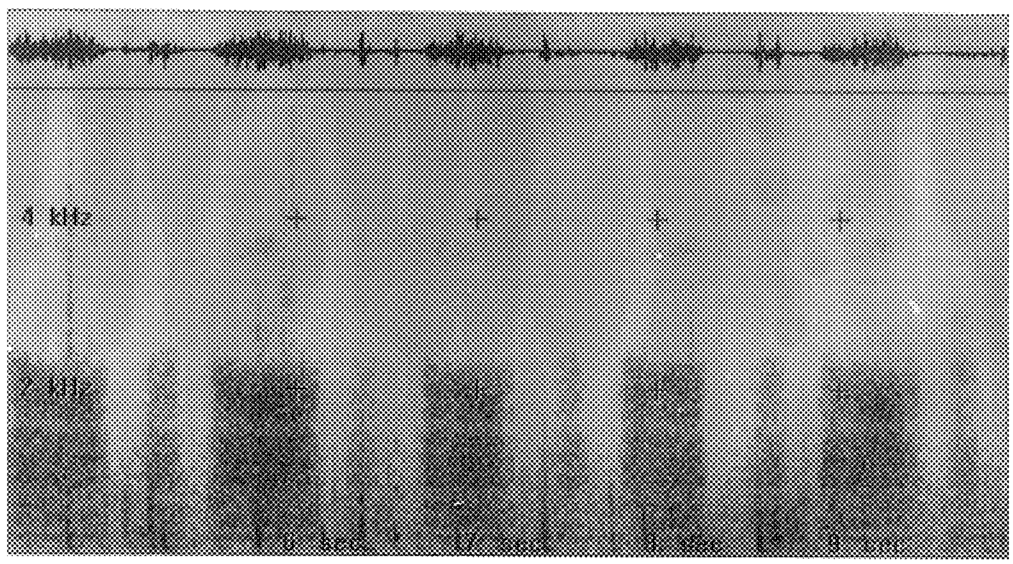
FIG. 10 shows a spectrogram of the upper respiratory sounds of a horse 100 with dorsal displacement of the soft palate (DDSP) exercising on a treadmill 110 at a speed corresponding to its maximum heart rate.
Figure 11:
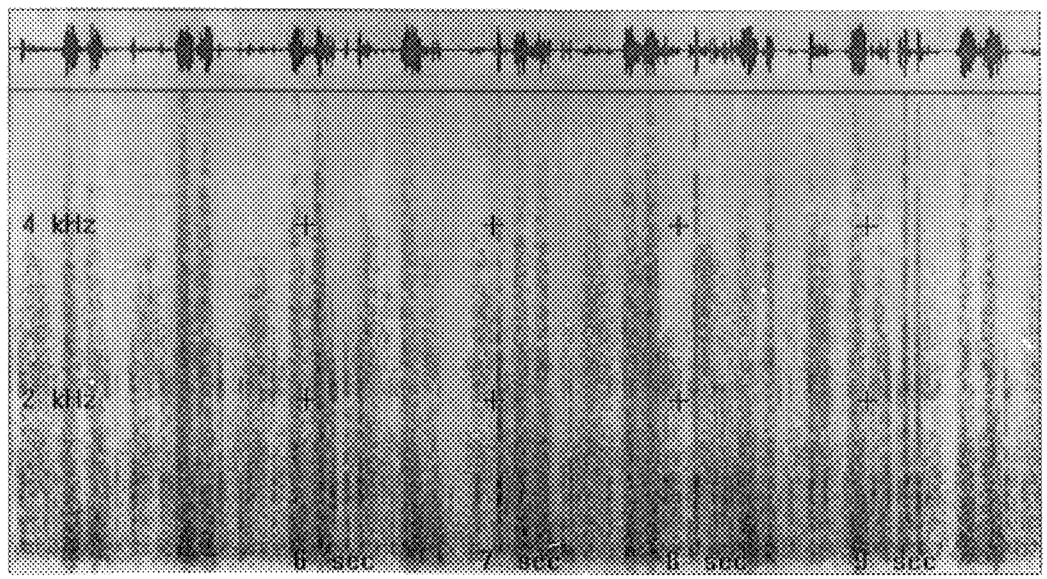
FIG. 11 shows a spectrogram of the upper respiratory sounds of a normal horse 100 exercising on a treadmill 110 at a speed corresponding to its maximum heart rate.

The spectrum analysis patterns associated with various upper airway obstructive conditions such as left laryngeal hemiplegia (LLH) and dorsal displacement of the soft palate (DDSP) are vastly different. The spectrogram of the respiratory sounds of a horse with LLH is shown in FIG. 9. The pattern is distinguishable from the spectrogram pattern of respiratory sounds of a horse with DDSP as shown in FIG. 10. Both the LLH and the DDSP spectrogram patterns are distinguishable from the spectrogram pattern for the respiratory sounds of a normal horse as shown in FIG. 11. The differences in the respiratory sounds and the corresponding spectrum analysis patterns are useful for making a diagnosis of a particular upper airway condition in a horse.

Spectrogram analysis of respiratory sounds in exercising horses has important applications. It appears that all of the upper respiratory conditions of horses are associated with unique spectrogram patterns. Simple recording of respiratory sounds under field conditions can yield a diagnosis of specific upper airway conditions, thereby avoiding the need for endoscopic examinations on a high-speed treadmill. Also, upper airway conditions in horses are associated with exercise intolerance and respiratory noise production.

An additional use of the recording unit of the present invention is to evaluate the efficacy of surgical procedures for treating upper airway conditions. Presently, the efficacy of surgical procedures to treat upper airway conditions is evaluated using measurements of air flows and driving pressures (Tetens et al., Am. J. Vet. Res. 57: 1668–1673 (1996); Shappell et al., Am. J. Vet. Res. 49: 1760–1765 (1988); Belknap et al., Am. J. Vet. Res. 51: 1481–1487 (1990)). Changes in respiratory sounds following surgical intervention provides very useful information.

In a series of studies, various surgical techniques for treating these upper airway conditions were evaluated to determine their ability to reduce upper airway impedance (Tetens et al., Ibid; Shappell et al., Ibid; Belknap et al., Ibid). However, reduction of upper airway impedance in affected horses did not necessarily reduce respiratory noise. For many owners, the respiratory noise associated with upper airway conditions is just as important as the upper airway obstruction. Spectrogram analysis of respiratory sounds in exercising horses recorded using any one of the embodiments of the recording unit herein now makes it possible to evaluate the efficacy of surgical techniques in reducing respiratory sounds associated with upper airway obstructive conditions.

The following example is intended to promote a further understanding of the present invention.

EXAMPLE 1

This example illustrates the use of the recording unit 10 (comprising the preferred cavesson) for detecting respiratory sounds in horses in which LLH and DDSP is experimentally induced.

Horses are studied under baseline conditions and after temporary induction of LLH and DDSP using well known local anesthetic techniques (Ehrlich et al., Vet. Surg. 24: 36–48 (1994); Holcombe et al., Am. J. Vet. Res. 59: 504–508 (1998)). Briefly, to induce LLH, 2 cc of local anesthetic is placed over the left recurrent laryngeal nerve as the nerve approaches the larynx. To induce DDSP, 2 cc of local anesthetic is placed bilaterally over the pharyngeal branches of the vagus nerve as they run through the guttural pouch. A randomized crossover design is used for the studies. Studies are separated by at least one week. The speed at which each horse reaches maximum heart rate is determined using a rapid incremental exercise test as described in Holcombe et al. (Ibid).

Directly prior to the experiments, the upper airway of each horse is examined using a fiber optic endoscope to ensure that the upper airway is functioning normally. Subsequently, the desired experimental condition is created (normal, LLH or DDSP) and verified by endoscopic examination. Next, the portable recording unit 10 is mounted on the horse 100.

Because the respiratory sounds of interest become manifest only when a horse 100 is exercising, sound recordings are made while the horse 100 is exercising at a speed corresponding to maximum heart rate speed either in the gallop, trot, or pace. The ambient noise was rendered harmless by two techniques.

First, the recording microphone 12 of the recording unit 10 is unidirectional and when the recording unit 10 is placed on the head 102 of the horse, the microphone 12 is preferably about 4.0 cm (1.6 inches) from the tip of the horse's nose 106 ("tight miked"). The microphone 12 is centered on the nose 106 between the nostrils 108 and, therefore, is not in the direct path of the horse's nasal exhalations and is not subject to blast effect. Nevertheless, the microphone 12 is still in close enough proximity to the nostrils 108 to detect the respiratory sounds.

The recorder 16 preferably has an automatic gain control. In this example, a Panasonic SLIMLINE® Model RQ2102 was used. The Panasonic SLIMLINE® Model RQ2102 recorder is designed for ready recording of speech in difficult environments such as conference rooms. The input section of the recorder 16 includes a strong compression circuit leading to a constant recording level that promotes intelligibility. The compression system in the recorder 16 is useful because the "tight-miked" exhalations of the horse 100 are intense enough and frequent enough to activate the recorder's compression feature and to squelch the ambient noise. The recorder 16 allows for recording the respiratory sounds from the horse 100 while squelching the environmental noises associated with the exercising horse 100. The microphone 12 was attached by the wire 20 to the recorder 16. The recorder 16 is mounted on the horse 100 or alternatively, mounted on a treadmill 110 similar to that shown in FIG. 5.

Once the portable recording unit 10 is in place, the horses are placed on the treadmill similar to that shown in FIG. 5. After a five minute warmup period, the horses 100 are exercised at maximum heart rate for two minutes. Endoscopic examination is repeated immediately following the exercise.

Pharyngeal pressure is measured using a pharyngeal catheter positioned at the level of the guttural pouch openings, as described in Holcombe et al. (Ibid). The pharyngeal pressure is used to determine the timing of inhalation and exhalation. The microphone 12 and recorder 16 are then activated. The respiratory sounds recorded on the recorder 16 are then analyzed using a computer based spectrogram program. A software program which can be used to analyze the respiratory sounds is AUDIO-SPECTRUM ANALYSIS™ or SPECTROGRAM VERSION 6™, shareware available from Visualization Software, LLC which is downloadable over the Internet at visualizationsoftware.com.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. An apparatus for recording respiratory sounds of an exercising horse which comprises:

(a) a microphone with a head which detects respiratory sounds at close proximity;

(b) a horse restraining apparatus comprising a nose-band and a cheek-piece with a top for going behind and around the ears of the horse which is mountable on the head of the horse and which includes a support means with a distal end and a proximal end wherein the microphone is securely mounted to the distal end of the support means and the proximal end of the support means is securely mounted on the nose-band of the horse restraining apparatus and wherein the support means enables the head of the microphone to be positioned between nostrils of the horse and without touching the horse so that the respiratory sounds at close proximity to the nostrils of the horse are detected; and (c) a recording means for recording the respiratory sounds detected by the microphone at close proximity to the nostrils of the horse wherein the recording means squelches other sounds at a distance from the nostrils.

2. The apparatus of claim 1 wherein a wire for transmitting the respiratory sounds detected by the microphone to the recording means extends from the microphone to the recording means along a path which is parallel to the support means mounted on the nose-band of the horse restraining apparatus and is parallel to the nose-band and the cheek-piece to the top of the cheek-piece and which extends from the top of the cheek-piece to the recording means.

3. The apparatus of claim 2 wherein the support means is a tube defined by at least one wall forming the tube in which the wire for transmitting the respiratory sounds extends therethrough.

4. The apparatus of claim 1, 2, or 3 wherein the microphone is unidirectional.

5. The apparatus of claim 1, 2, or 3 wherein the recording means has a compression circuit which allows for a constant recording level of the sounds at close proximity to the nostrils of the horse.

6. The apparatus of claim 1 wherein the microphone includes a wireless transmitter for transmitting the respiratory sounds to a wireless receiver in the recording means.

7. The apparatus of claim 1 wherein the microphone includes a wireless transmitter for transmitting the respiratory sounds to a wireless receiver in a computer for analyzing the respiratory sounds in real time.

8. The apparatus of claim 1 wherein the horse restraining apparatus is selected from the group consisting of cavessons, bridles, bitless bridles, and halters.

9. A method for recording and analyzing respiratory sounds of an exercising horse to detect an airway condition which comprises:

(a) providing an apparatus for analyzing respiratory sounds of an exercising horse which comprises:

(1) a microphone with a head which detects respiratory sounds at close proximity;

(2) a horse restraining apparatus comprising a nose-band and a cheek-piece with a top for going behind and around the ears of the horse which is mountable on the head of the horse and which includes a support means with a distal end and a proximal end wherein the microphone is securely mounted to the distal end of the support means and the proximal end of the support means is securely mounted on the nose-band of the horse restraining apparatus and wherein the support means enables the head of the microphone to be positioned between nostrils of the horse and without touching the horse so that the respiratory sounds at close proximity to the nostrils of the horse are detected; and (3) a recording means for recording the respiratory sounds detected by the microphone at close proximity to the nostrils of the horse and squelching other sounds at a distance from the nostrils;

(b) mounting the apparatus on the head of the horse and positioning the head of the microphone to be adjacent to the nostrils of the horse;

(c) recording the respiratory sounds detected by the head of the microphone with the recording means; and (d) analyzing the respiratory sounds recorded on the recording means to detect the condition.

10. The method of claim 9 wherein a wire for transmitting the respiratory sounds detected by the microphone to the recording means extends from the microphone to the recording means along a path which is parallel to the support means mounted on the nose-band of the horse restraining apparatus and is parallel to the nose-band and the cheek-piece to the top of the cheek-piece and which extends from the top of the cheek-piece to the recording means.

11. The method of claim 10 wherein the support means is a tube defined by at least one wall forming the tube in which the wire for transmitting the respiratory sounds extends therethrough.

12. The method of claim 9 wherein the microphone includes a wireless transmitter for transmitting the respiratory sounds to a wireless receiver in the recording means.

13. The method of claim 9 wherein the microphone includes a wireless transmitter for transmitting the respiratory sounds to a wireless receiver in a computer for analyzing the respiratory sounds in real time.

14. The method of claim 9, 10, 11, 12, or 13 wherein the analysis is for laryngeal hemiplegia and dorsal displacement of the soft palate.

15. The method of claim 9, 10, 11, 12, or 13 wherein a computer program produces a graph of the respiratory sounds for analyzing in step (d).

16. The method of claim 9 wherein the horse restraining apparatus is selected from the group consisting of cavessons, bridles, bitless bridles, and halters.

17. The method of claim 9, wherein the airway condition is an upper airway obstructive condition.

* * * * *